US008337427B2

(12) United States Patent
Tsuji et al.

(10) Patent No.: US 8,337,427 B2
(45) Date of Patent: Dec. 25, 2012

(54) METHOD OF ESTIMATING FINGER-TAPPING FORCE

(75) Inventors: Toshio Tsuji, Higashi-hiroshima (JP); Keisuke Shima, Higashi-hiroshima (JP); Yasuhiro Tamura, Higashi-hiroshima (JP); Akihiko Kandori, Tokyo (JP); Yuko Sano, Kokubunji (JP); Tsuyoshi Miyashita, Tsurugashima (JP)

(73) Assignee: Hitachi Consumer Electronics Co., Ltd., Tokyo (JP)

( * ) Notice: Subject to any disclaimer, the term of this patent is extended or adjusted under 35 U.S.C. 154(b) by 332 days.

(21) Appl. No.: 12/604,515

(22) Filed: Oct. 23, 2009

(65) Prior Publication Data
US 2010/0106060 A1      Apr. 29, 2010

(30) Foreign Application Priority Data
Oct. 23, 2008   (JP) .................................. 2008-273397

(51) Int. Cl.
*A61B 5/117*   (2006.01)
*A61B 5/103*   (2006.01)

(52) U.S. Cl. ...................................................... 600/587
(58) Field of Classification Search .................. 600/300, 600/587, 595; 345/418, 158; 178/18.01
See application file for complete search history.

(56) References Cited

U.S. PATENT DOCUMENTS

| | | |
|---|---|---|
| 2005/0065422 A1 | 3/2005 | Kandori et al. |
| 2006/0244744 A1 | 11/2006 | Kandori et al. |
| 2007/0038067 A1 | 2/2007 | Kandori et al. |
| 2007/0272599 A1 | 11/2007 | Miyashita et al. |
| 2008/0238414 A1 | 10/2008 | Miyashita et al. |

FOREIGN PATENT DOCUMENTS
JP      3841075      8/2006

*Primary Examiner* — Brian Szmal
(74) *Attorney, Agent, or Firm* — Antonelli, Terry, Stout & Kraus, LLP.

(57) ABSTRACT

In a bioinstrument system S of the present invention, a processor unit 121 in a bioinstrument device 108 obtains information indicative of displacement of two fingers in deformed state from distance between the two fingers; and calculates a finger-tapping force by using the obtained information and a predetermined fingertips' stiffness function retrieved from a storage unit 122. This provides a method for inspecting for neurological disorders in consideration of the finger-tapping force.

3 Claims, 17 Drawing Sheets

TIME[sec.]

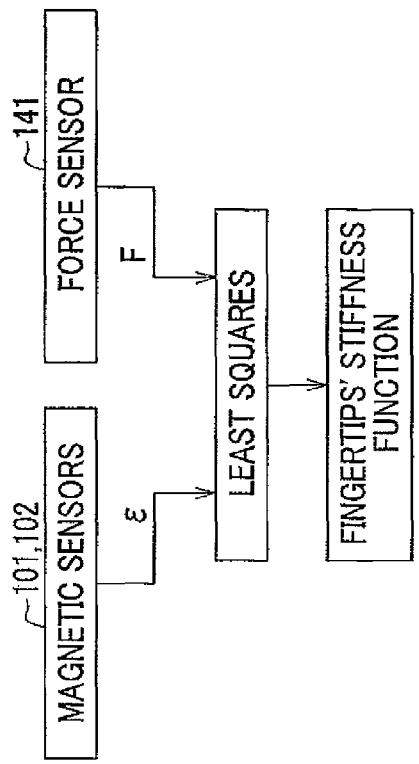
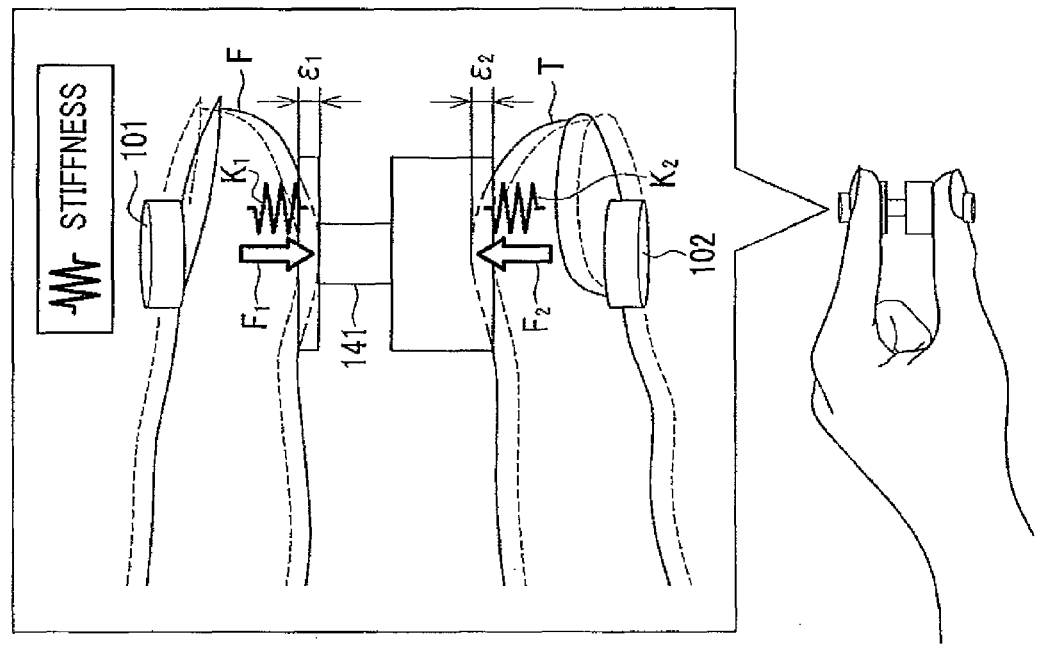
FIG.5A
FIG.5B

ESTIMATION OF FINGER-TAPPING FORCE

MEASUREMENT RESULT OF TAPPING FORCE
AND DISPLACEMENT OF FINGERTIPS' DISTANCE

CORRELATION BETWEEN DISPLACEMENT OF FINGERTIPS' DISTANCE
AND TAPPING FORCE

SLIGHTLY DIFFERENT TAPPING FORCES VARYING OVER DISPLACEMENT OF FINGERTIPS' DISTANCE
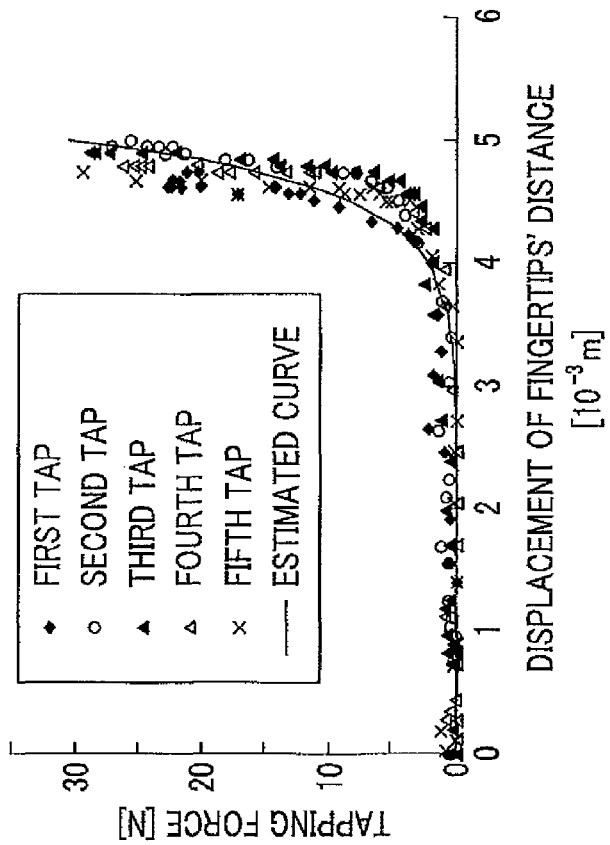
FIG.9A WITH STRONGER TAPPING FORCE
FIG.9B WITH WEAKER TAPPING FORCE

CORRELATION BETWEEN MEASURED TAPPING FORCE AND ESTIMATED TAPPING FORCE

WITH STRONGER TAPPING FORCE

WITH WEAKER TAPPING FORCE

ENLARGED VIEW (WITH WEAKER TAPPING FORCE)

ENLARGED VIEW (WITH SLIGHTLY STRONGER TAPPING FORCE)

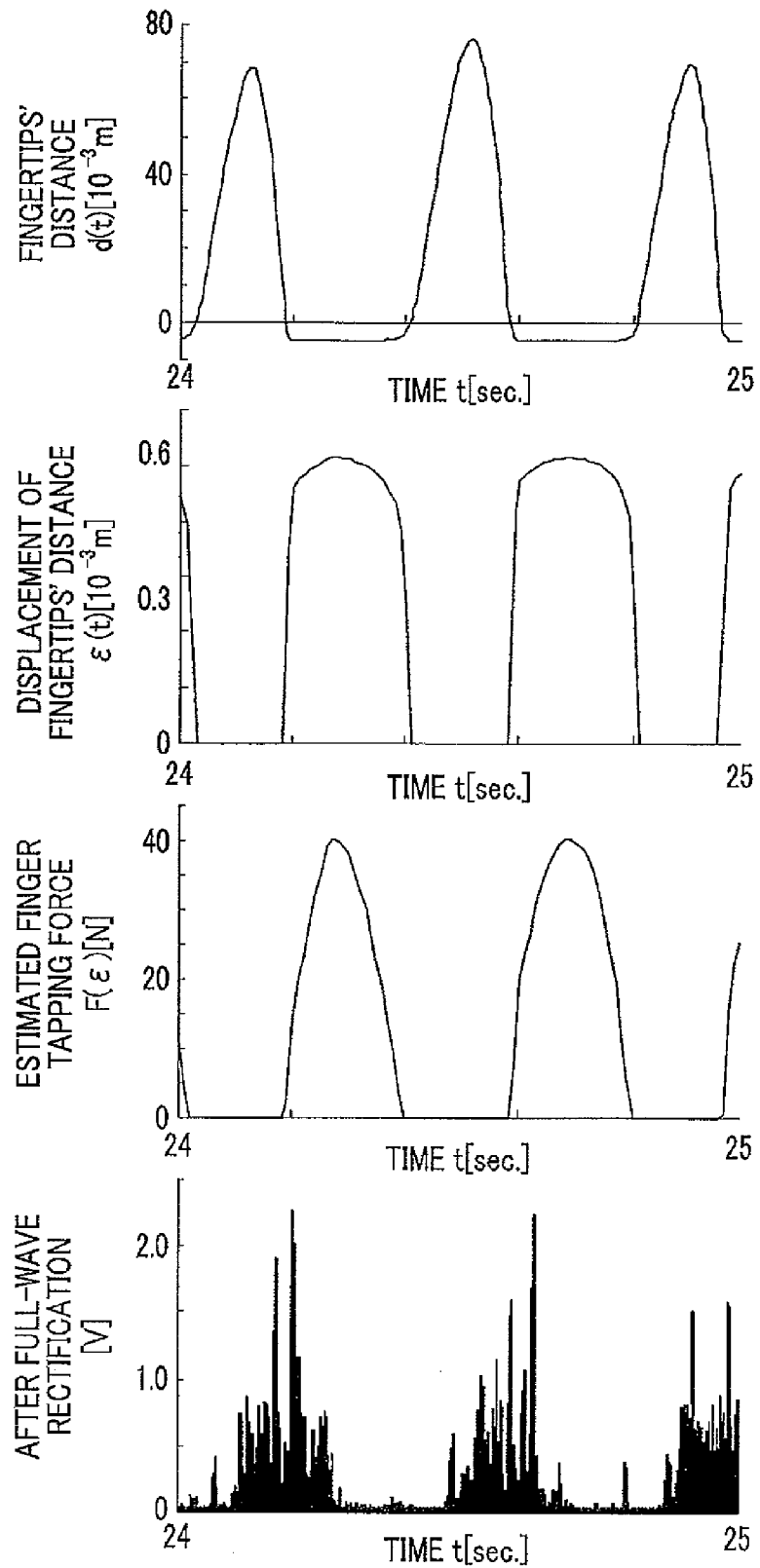

ENLARGED VIEW (WITH SLIGHTLY STRONGER TAPPING FORCE)

ENLARGED VIEW (WITH STRONGER TAPPING FORCE)

METHOD OF ESTIMATING FINGER-TAPPING FORCE

BACKGROUND OF THE INVENTION

1. Field of the Invention

The present invention relates to a technology of inspection for neurological disorder etc.

This application claims the foreign priority benefit under Title 35, United States Code, §119 (a)-(d), of Japanese Patent Application No. 2008-273397, filed on Oct. 23, 2008, in the Japan Patent Office, the disclosure of which is herein incorporated by reference in its entirety.

2. Related Art

In recent years, a rapidly increasing number of patients (hereinafter called "neurological disorder patients") suffer from neurological disorders e.g. Parkinson's disease or cerebral apoplexy in Japan. For example, Parkinson's disease has four major symptoms: tremor; muscle rigidity (i.e. continuous involuntary sustained muscle contraction); postural instability (i.e. impaired balance and coordination); and bradykinesia (i.e. slowing of physical movement). Human movement is controlled by a brain which emits a bioelectric instruction signal of making body movement, and the body movement is realized by muscle which contracts upon receiving the bioelectric instruction signals through the nervous system. However, a neurological disorder patient exhibits abnormal movement or coordination since a bioelectric instruction signal emitted from a brain and instructing for making body movement cannot be transmitted through a nervous system accurately.

The rapidly growing number of neurological disorder patients may lead to not only increased medical cost but also huge social loss since these patients are hardly employable. Therefore, in order to solve a social problem caused by these neurological disorders, we must be able to accurately determine whether a test subject person (hereinafter called subject person) suffers from a neurological disorder or not, and to what degree the neurological disorder has progressed if the person is ailing.

However, the fact of ailment and degree of its progression cannot be determined by hemanalysis, or image diagnosis obtained by using Magnetic Resonance Imaging (MRI) since a neurological disorder patient is not distinguishable from a non-diseased person. Therefore, in many cases, the fact of ailment and degree of its progression are determined based on subjective view of an inspector, e.g. a doctor, empirically or based on his or her insight. In consideration of such a background, finger movement tests are widely used to monitor fingertips' movement of a person for evaluating to what degree his or her motility has decreased and how seriously his or her autonomic nerve system is dysfunctional due to Parkinson's disease.

In order to monitor the fingertips' movement, various methods are conceived using an electric switch, a metal loop, a keyboard, or a three-dimensional camera. However, these methods are used not so widely because none of them can be carried out easily.

To address this situation, the applicant of the present application formerly proposed a bioinstrument device which uses magnetic sensors and is capable of detecting human body movement, e.g., continuous tapping movement (hereinafter called finger-tapping movement) of two fingers, e.g. the thumb and the forefinger of one of test subject person's hands) (see Japan Patent No. 3,841,075, hereinafter called Patent Document 1). The technology disclosed in Patent Document 1 is capable of determining whether a person is a neurological disorder patient or a non-diseased person very accurately by analyzing information obtained from the finger-tapping movement to recognize the two fingers' movement of the subject person.

However, whether the subject person is a neurological disorder patient or a non-diseased person cannot be determined in consideration of the finger-tapping force since a pushing force produced in the finger-tapping movement by the two fingers is not obtainable in the technology disclosed in Patent Document 1. In many cases, a neurological disorder patient shakes or grips an article with a significantly weaker force than that of a non-diseased person. The applicant believes that a finger-tapping force is significantly different between a neurological disorder patient and a non-diseased person even though a two fingers' movements resemble between the neurological disorder patient and the non-diseased person.

SUMMARY OF THE INVENTION

In consideration of the aforementioned circumstances, it is an object of the present invention to provide a method for inspecting neurological disorders etc. capable of considering a finger-tapping force, which is a pushing force produced between two fingers upon making contact with each other in the finger-tapping movement.

The present invention provides a method for estimating a finger-tapping force in a finger-tapping movement of two fingers of one of a subject person's hands by using a bioinstrument device, the finger tapping force being a pushing force of the two fingers upon making contact with each other, wherein the bioinstrument device comprises: a detector unit for detecting movement information relating to one of distance between the two fingers, relative velocity of the two fingers, and relative acceleration of the two fingers; an input unit which receives the movement information from the detector unit; a processor unit for calculating the finger-tapping force based on the movement information inputted into the input unit; and a storage unit having at least a predetermined fingertips' stiffness function stored therein, the predetermined fingertips' stiffness function indicating a correlation between the finger-tapping force and displacement of the two fingers in deformed state, and wherein the method comprising the steps, conducted by the processor unit, of: calculating the distance between the two fingers based on the movement information obtained from the detector unit through the input unit; obtaining information indicative of the displacement of the two fingers in the deformed state, the displacement being included in the calculated distance of the two fingers; calculating the finger-tapping force by using the information indicative of the displacement and the predetermined fingertips' stiffness function retrieved from the storage unit.

The present invention can provide a method for inspecting neurological disorders etc. capable of considering a finger-tapping force.

BRIEF DESCRIPTION OF THE DRAWINGS

FIGS. 5A and 5B show a method for estimating a finger-tapping force in the present embodiment.

FIGS. 9A and 9B are profiles of two slightly different tapping forces each obtained in five taps and varying over the displacement of the fingertips' distance.

FIG. 11D shows graphs of the parameters described in the portion of the time frame shown in FIG. 11A and obtained with a "strong" tapping force.

DETAILED DESCRIPTION OF THE INVENTION

The best mode (hereinafter called "embodiment") for carrying out the present invention will be explained in detail with reference to the accompanying drawings.

<Overall Structure>

Figure 1:
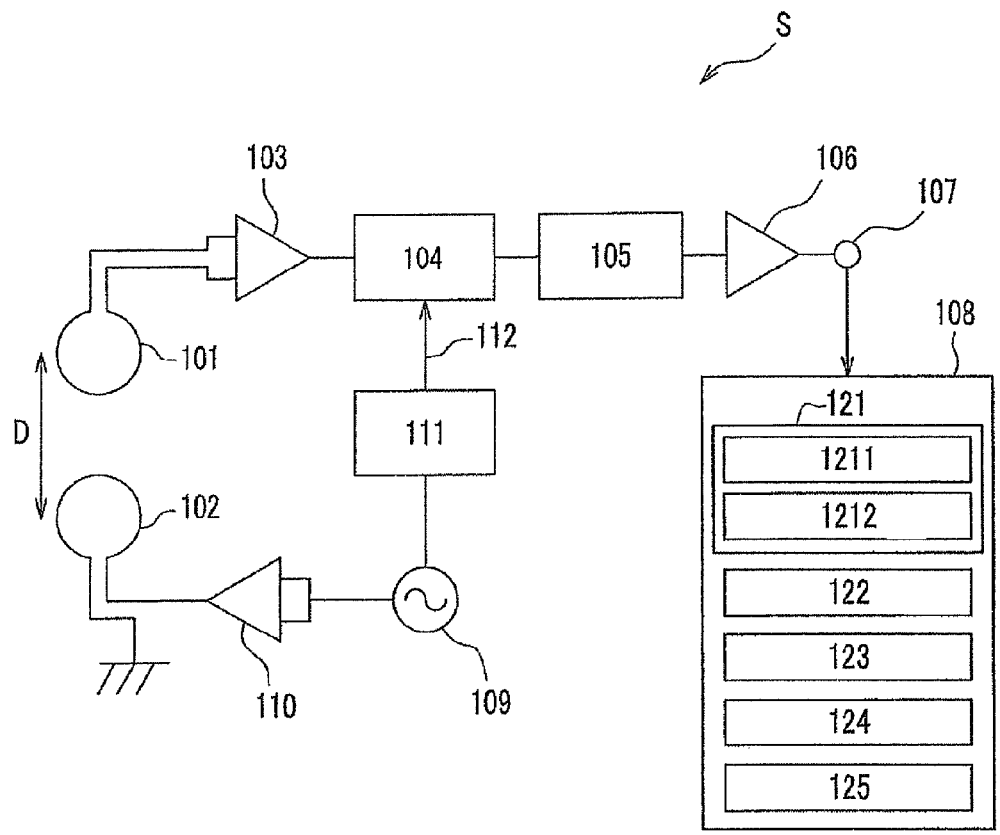
FIG. 1 is a schematic diagram of a bioinstrument system according to an embodiment of the present invention.

FIG. 1 is a schematic diagram of a bioinstrument system according to an embodiment of the present invention. Each unit included in the system will be explained in detail in accordance with order of operations conducted in the present embodiment.

An AC oscillator circuit 109 produces an alternating current (hereinafter called AC current) having a predetermined frequency of 20 kHz etc. An electric-current-producing amplifier circuit 110 amplifies the AC current produced by the AC oscillator circuit 109 and having the predetermined frequency. The AC current amplified by the electric-current-producing amplifier circuit 110 flows through an oscillator coil of a magnetic sensor 102 which serves as a detector unit. The AC current flowing through the oscillator coil of the magnetic sensor 102 produces a magnetic field. The magnetic field induces an electromotive force in a receiver coil of a nearby magnetic sensor 101 which serves as a detector unit. The magnetic sensor 102 is attached to the thumb of one of a subject person's hands, and the magnetic sensor 101 is attached to the forefinger of the same hand. These sensors will be explained later in detail with reference to FIG. 2. Hereinafter the thumb and the forefinger, each having the sensor attached thereon, will be called "two fingers".

The electromotive force induced in the receiver coil of the magnetic sensor 101 has the same frequency as that of the AC current produced by the AC oscillator circuit 109. A pre-main amplifier circuit 103 amplifies the electromotive force, and a demodulation circuit 104 receives a signal indicative of the amplified electromotive force. The demodulation circuit 104 demodulates the received signal by using the predetermined frequency of the AC current produced in the AC oscillator circuit 109, or by using its doubled frequency. A phase-control circuit 111 controls the phase of the AC current outputted from the AC oscillator circuit 109, and sends out a reference signal 112 to a reference-signal-receiving terminal of the demodulator circuit 104.

The phase-control circuit 111 can be omitted if demodulation is conducted by using the doubled frequency of the predetermined frequency. For example, in a simplified demodulation using the doubled frequency, the AC oscillator circuit 109 may double the predetermined frequency and reduce the doubled frequency to the half by using a frequency-dividing period, and may send it to the electric-current-producing amplifier circuit 110; and then, the phase-control circuit 111 may send the reference signal 112 having the doubled frequency of the predetermined frequency to the reference-signal-receiving terminal of the demodulator circuit 104.

The demodulator circuit 104 outputs a signal to a low-pass filter (LPF) circuit 105. An amplifier circuit 106 amplifies the signal to a predetermined voltage and sends the amplified signal as an output signal 107 to a bioinstrument device 108. The output signal 107 has a voltage indicative of distance D between the magnetic sensor 102 attached to the thumb and the magnetic sensor 101 attached to the forefinger.

The bioinstrument device 108 is a computer device for recording or analyzing the output signal 107. The bioinstrument device 108 includes a processor unit 121; a storage unit 122; an information receiver unit 123; a display unit 124; and a signal receiver section 125.

The processor unit 121, e.g. a Central Processing Unit (CPU) having a fingertips'-displacement-calculating unit 1211 and a finger-tapping-force-estimating unit 1212 conducts mechanical analysis of the finger-tapping movement of a subject person and displays the analyzed result etc. on the display unit 124.

The fingertips'-displacement-calculating unit 1211 calculates displacement of the two fingers, i.e. the distance between the two fingers and the variation thereof based on the output signal 107. (It should be noted that the detail of the fingertips'-displacement-calculating unit 1211 will be explained later.)

The finger-tapping-force-estimating unit 1212 calculates the finger-tapping force (i.e., the pushing force produced by the two fingers upon making contact with each other in the finger-tapping movement) by using information indicative of displacement of the two fingers in a deformed state and a predetermined fingertips' stiffness function, both of which are calculated by the fingertips'-displacement-calculating unit 1211. (It should be noted that the detail of the finger-tapping-force-estimating unit 1212 will be explained later.)

As far as the processor unit 121 is concerned, it should be noted hereinafter that, functions other than those conducted by the fingertips'-displacement-calculating unit 1211 and the finger-tapping-force-estimating unit 1212 are be conducted by the processor unit 121.

The storage unit 122 is a storage device or a temporary storage device for storing various programs, data, analyzed result, and predetermined fingertips' stiffness function (the detail of which will be explained later). For example, the storage unit 122 may be a read-only memory (ROM), a random access memory (RAM), or a hard-disk drive unit etc. The processor unit 121 is capable of conducting various operations by using programs and data etc. stored in the storage unit 122, and storing data and analyzed result etc. in the storage unit 122.

The information receiver unit 123 may be, e.g. a keyboard or a mouse etc. into which an operator of the bioinstrument device 108 can input information regarding the subject person. The information receiver unit 123 may have a function of graphical user interface (GUI).

The display unit 124 may be, e.g. a liquid crystal display (LCD) or a cathode ray tube (CRT) display unit for displaying data or analyzed result produced by the processor unit 121.

The signal receiver section 125 is an interface for receiving the output signal 107 outputted from the amplifier circuit 106.

Figure 2:
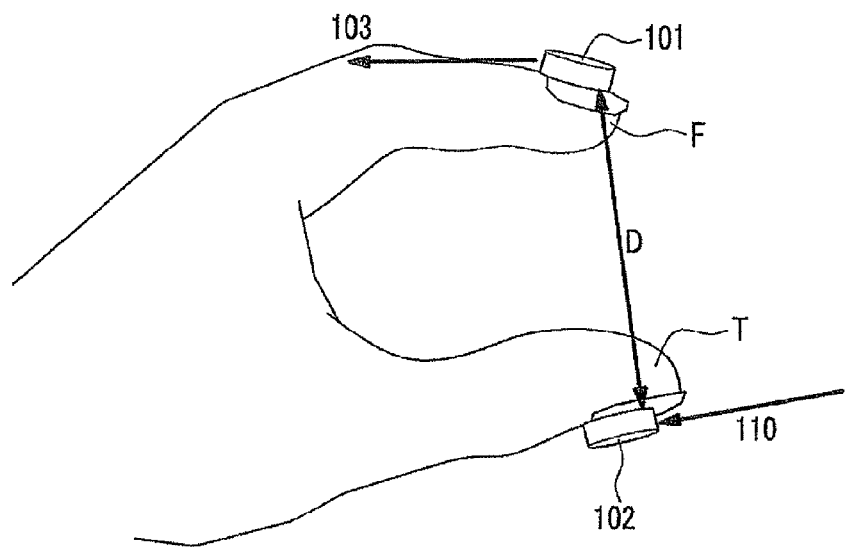
FIG. 2 shows magnetic sensors attached to one of a subject person's hands.

FIG. 2 shows the magnetic sensors 101 and 102 attached to one of the subject person's hands (left hand in this case).

As shown in FIG. 2, the magnetic sensor 102 connected to the electric-current-producing amplifier circuit 110 is fixed on the thumb T via a double-sided adhesive tape (not shown in the drawing).

The magnetic sensor 101 connected to the pre-main amplifier circuit 103 is fixed on the forefinger F via a double-sided adhesive tape in the same manner (not shown in the drawing).

It should be noted that, the present invention does not limit the method of fixing the magnetic sensors 101 and 102 onto the fingers to the example shown in FIG. 2. The sensors may be fixed by using a piece of (or several pieces of) resin-made band etc.

The present invention can determine the distance D within a tolerance of plus or minus about 2% in accordance with the voltage of the output signal 107, by using the aforementioned fixing method and predetermined correlation between the distance D between the magnetic sensor 102 and the magnetic sensor 101 and the voltage of the output signal 107 stored in the storage unit 122 of the bioinstrument device 108. It should be noted that the magnetic sensors 101 and 102 may be fixed to two fingers other than the aforementioned thumb T and the forefinger F in the present invention.

Figure 3:
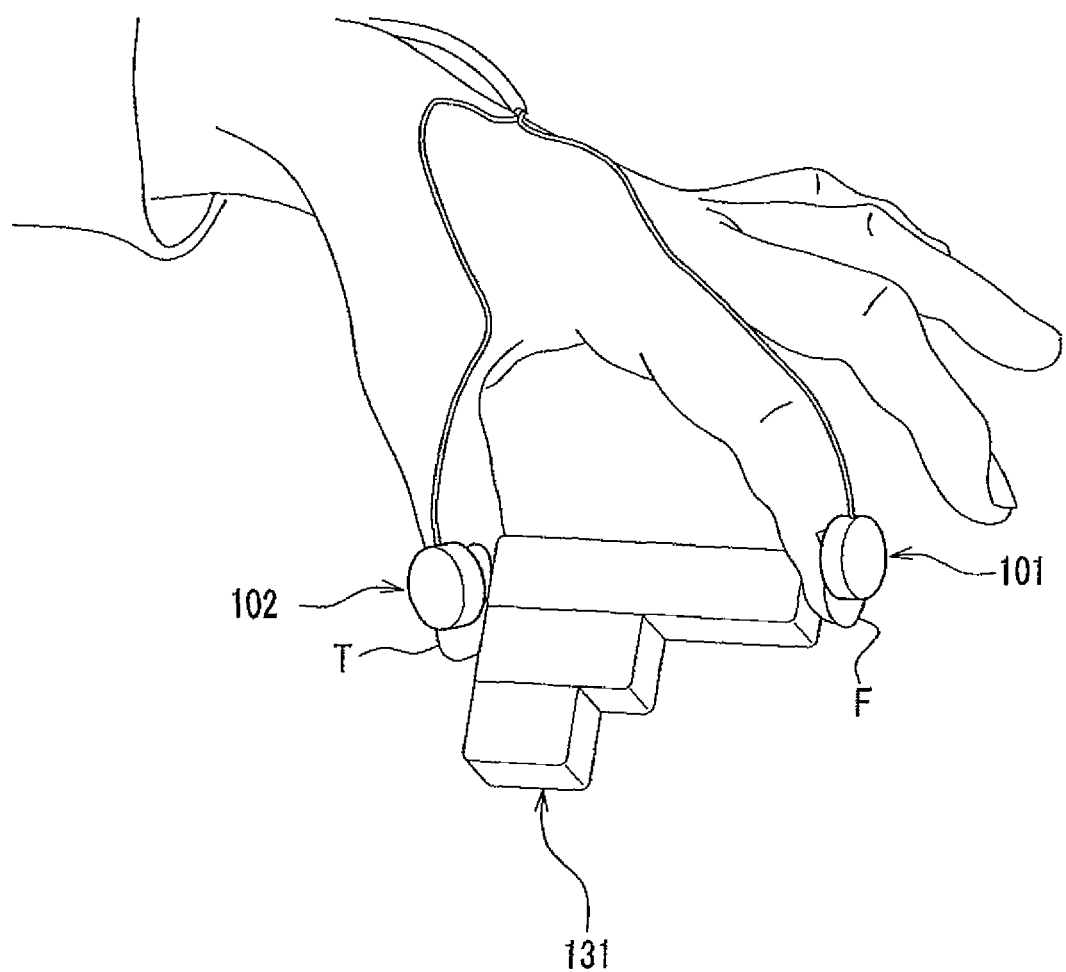
FIG. 3 is a perspective view showing a thumb and a forefinger of a subject person grasping a calibration block.

FIG. 3 is a perspective view showing the thumb T and the forefinger F of the subject person holding a calibration block 131. The calibration block 131 is a calibration instrument. Different finger sizes among a plurality of subject persons can be calibrated by holding the calibration block 131 with a thumb and a forefinger of each subject person; measuring the length of the calibration block 131 held in this state; and obtaining information of the corresponding voltage.

As shown in FIG. 3, the calibration block 131 includes three kinds of rectangular parallelepiped blocks having different longitudinal lengths e.g. about 20 mm, about 30 mm, and about 60 mm and having the same width and thickness. These three rectangular parallelepiped blocks are arranged side by side in the direction which is orthogonal to the longitudinal lengths. In the present embodiment, the subject person should preferably hold the calibration block 131 by using the thumb and the forefinger not strongly, i.e. weakly so that the two fingers may not be deformed.

It should be noted that a calibration method conducted in the present invention is not limited to using the aforementioned calibration block 131. For example, the present invention may use an apparatus of another kind, e.g. a calibration data detector apparatus using variable resistors.

Figure 4A:
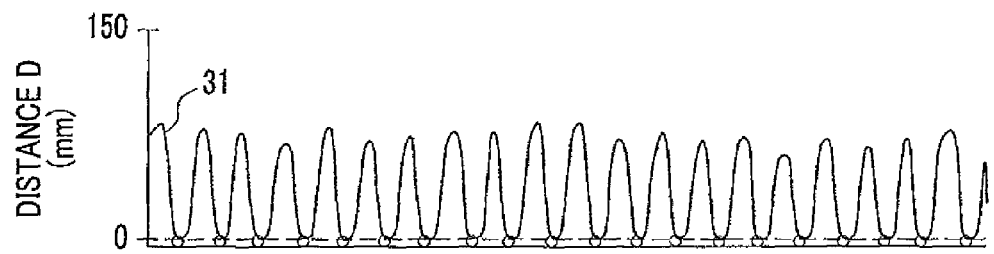
FIGS. 4A to 4C show examples of information obtained from the subject person conducting the finger-tapping movement.
Figure 4B:
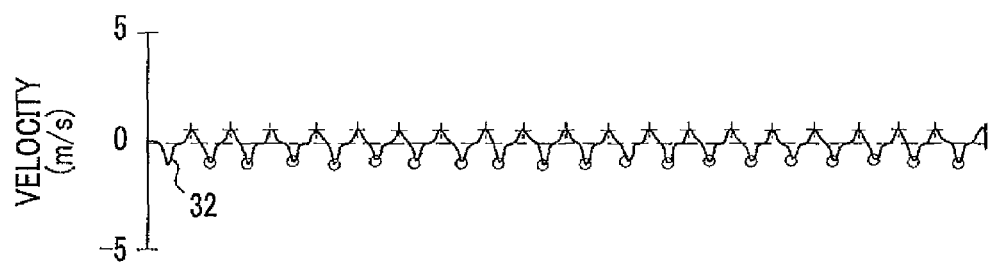
Figure 4C:
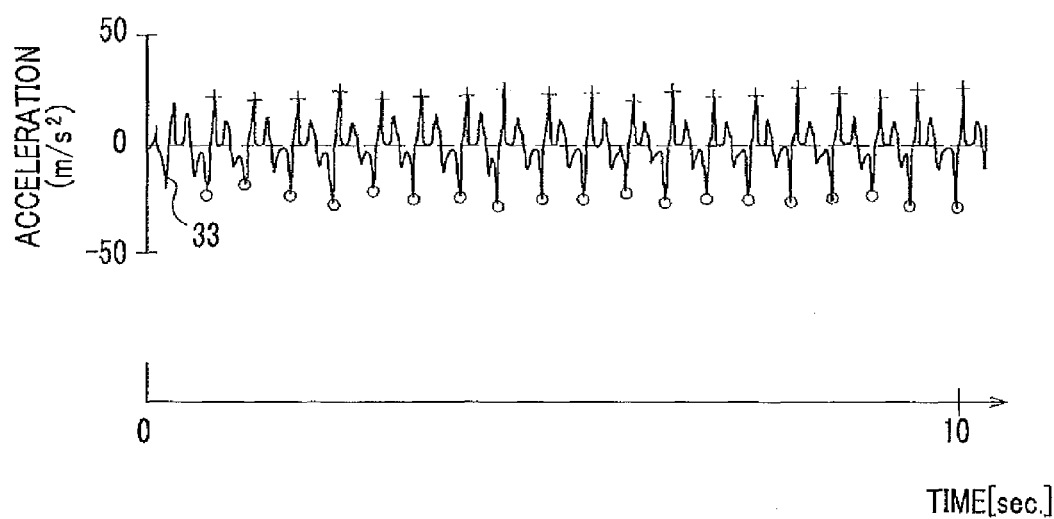

FIGS. 4A to 4C show examples of information obtained from a subject person conducting the finger-tapping movement. FIG. 4 shows correlation between time and distance between the two fingers. FIG. 4B shows correlation between time and velocities of the two fingers (hereinafter called relative velocity). FIG. 4C shows correlation between time and accelerations of the two fingers (hereinafter called relative acceleration). Hereinafter, a basic operation for processing information obtained from the finger-tapping movement will be explained with reference to FIGS. 4A to 4C; and an information-processing operation in consideration of deformation of the two fingertips will be explained with reference to FIG. 5A (and subsequent drawings if necessary).

FIG. 4A shows a profile of waveform 31 indicative of distance D (mm) of the two fingers over time. Circles "○" each put at a dip in the waveform 31 indicate the moments at which the distance D is 0 (zero), i.e. the two fingers make contact with each other at each moment. The fingertips'-displacement-calculating unit 1211 of the processor unit 121 in the bioinstrument device 108 produces the waveform 31 by converting the voltage of the output signal 107 to distance.

FIG. 4B shows a profile of waveform 32 indicative of velocity (m/s) of the two fingers over time where crosses "+" each put at a positive peak point in the waveform 32 indicate that the velocity of the two opening fingers is at maximum there; and circles "○" each put at a negative peak point in the waveform 32 indicate that the velocity of the two closing fingers is at minimum there. That is, as far as velocity and acceleration are concerned, the positive direction in the graphs indicates that the fingers are in an opening state. The processor unit 121 of the bioinstrument device 108 produces the waveform 32 by obtaining a time differential of the two fingertips' distance D shown by the waveform 31. It should be noted that the relative velocity is 0 (zero) m/s at the moment at which the two fingers make contact with each other. The relative velocity is 0 (zero) m/s also at the moment at which the two fingers are in the full opening state.

FIG. 4C shows a profile of waveform 33 indicative of acceleration (m/s$^2$) of the two fingers over time where crosses "+" each put at a positive peak point in the waveform 33 indicate that the acceleration of the two opening fingers is at maximum there; and circles "○" each put at a negative peak point in the waveform 33 indicate that the acceleration of the two closing fingers is at minimum there. The processor unit 121 of the bioinstrument device 108 produces the waveform 33 by obtaining a time differential of the two fingers' velocity shown by the waveform 32.

Hereinafter, the waveforms indicative of distance, velocity, and acceleration are collectively called as "movement waveform". Alternatively, a strain gauge or an accelerometer used in place of the magnetic sensors 101 and 102 may obtain another complementary movement waveform if at least one movement waveform is previously measured by using the strain gauge or the accelerometer, and if the measured movement waveform is differentiated or integrated (see Patent Document 1 for the detail of the production of movement waveforms).

As shown in FIG. 2, a subject person puts the magnetic sensor 102 on the thumb T and the magnetic sensor 101 on the forefinger F, and then the distance between the magnetic sensors 101 and 102 in this state is measured. It should be noted that the magnetic sensor 102 or the magnetic sensor 101 may be put on either one of the thumb T and the forefinger F; and the sensors may be put not on the nails of these fingers.

A magnetic field produced around the magnetic sensor 102 and having a frequency of 20 kHz induces an electromotive force around the magnetic sensor 101. The demodulator circuit 104 detects the induced electromotive force. After that, the demodulator circuit 104 conducts a lock-in demodulation of the detected electromotive force and obtains frequency components in the vicinity of 20 kHz. The bioinstrument device 108 converts the demodulated electromotive force outputted from the demodulator circuit 104 to a distance between the two fingers. This operation has been explained previously in detail with reference to FIG. 1.

The subject person conducts the finger-tapping movement in sitting and relaxed position. The finger-tapping movement may be conducted in various ways: periodical inspection may be one way in which the fingers are tapped at a frequency of 1 to 5 Hz provided by using a metronome; and non-periodic inspection may be another way in which the fingers are tapped not at a predetermined frequency. It should be noted that the subject person in the non-periodic inspection should be instructed more specifically, i.e. to tap fingers "as fast and wide as possible", "as fast as possible", or "as wide as possible" etc. In this case, the tapping frequency will be at about 2 to 5 Hz.

<Method for Estimating Finger-Tapping Force>

Hereinafter, a method (hereinafter called "present method") for estimating the finger-tapping force using the magnetic sensors according to the present embodiment will be explained with reference to FIGS. 5A to 6. After that, experiment for proving reliability of estimated finger-tapping force and evaluating the effectiveness of the present method will be explained with reference to FIGS. 7 to 12D.

Figure 5C:
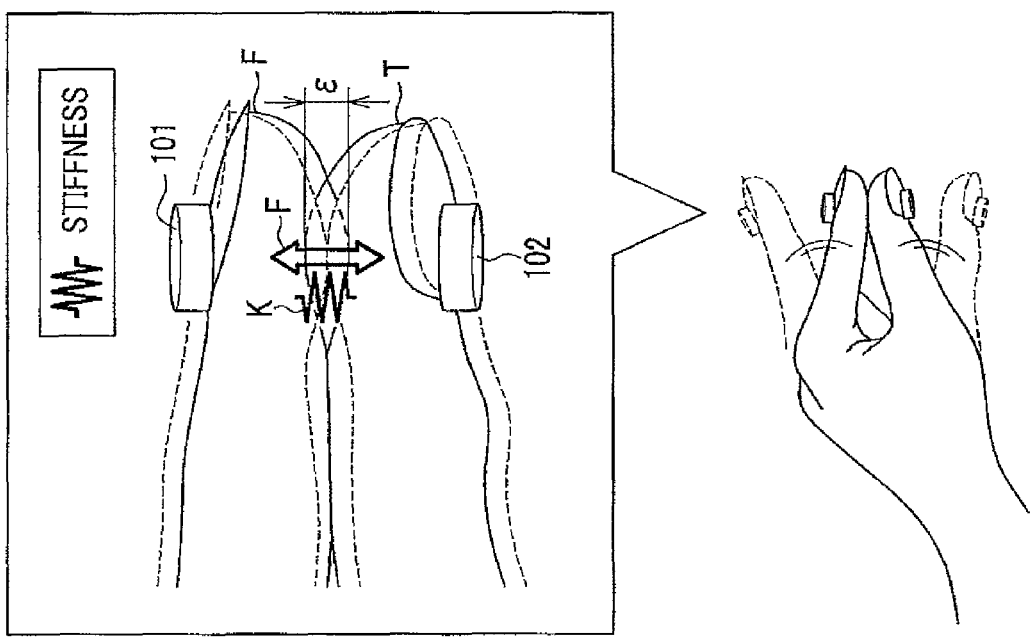
FIGS. 5C and 5D show a method for estimating a finger-tapping force in the present embodiment.

FIGS. 5A and 5B show the method for estimating the finger-tapping force in the present embodiment. In the present method, the stiffness characteristics of finger pulps of the subject person's two fingers (i.e. fingertips' stiffness function) are estimated by using the magnetic sensors 101 and 102 and a force sensor 141 (see FIGS. 5A and 5B); and after that, the finger-tapping force produced when the fingers are tapped is estimated based on the estimated stiffness characteristics (i.e. the fingertips' stiffness function) and the degree of the displacement of the two fingers measured by using the magnetic sensors 101 and 102 (see FIGS. 5C and 5D).

As shown in FIG. 5A, the subject person puts the magnetic sensors 101 and 102 on the thumb T and the forefinger F, and holds the force sensor 141 between the two fingers with a weak force not deforming the finger pulps thereof. When forces are applied to this state of the two fingers in approaching directions, displacement $\epsilon_1$ and a force $F_1$ occur on the finger pulp of the forefinger F, and displacement $\epsilon_2$ and a force $F_2$ occur on the finger pulp of the thumb T. They can be measured by using the magnetic sensors 101 and 102. The displacement c of the two fingertips' distance, which is identical with the displacement of the nails of the two fingers, is represented by the following equation (1):

$$\epsilon = \epsilon_1 + \epsilon_2 \quad \text{Equation (1)}$$

A force F measured by using the force sensor 141 in this state can be approximated as shown in the following equation (2):

$$F = F_1 + F_2 \approx K_1(\epsilon_1)\epsilon_1 + K_2(\epsilon_2)\epsilon_2 \quad \text{Equation (2)}$$

where $K_1$ and $K_2$ are stiffness parameters

The equation (2) can be modified to the following equation (3) by assuming that $K_1 = K_2 = K$, and $\epsilon_1 = \epsilon_2 = \epsilon/2$:

$$F \approx K(\epsilon/2)\epsilon \quad \text{Equation (3)}$$

The present method will be further explained with reference to FIG. 5B. At first, the subject person is instructed to apply forces to the two fingers holding the force sensor 141 therebetween, and then, the force F is measured by using the force sensor 141, and the displacement E is measured by using the magnetic sensors 101 and 102. A fingertips' stiffness function $K(\epsilon/2)$, indicative of correlation between the finger-tapping force and the displacement, can be estimated (or produced) by conducting a mathematic approach, e.g. least squares to the data including the force F and the displacement c.

Figure 5D:
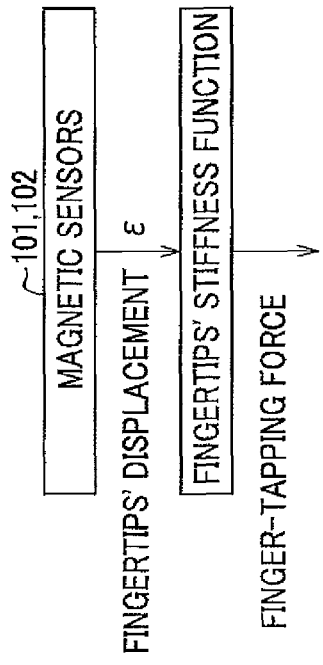

A method will be explained with reference to FIG. 5C, for estimating the finger-tapping force from the sum of displacements of the thumb T and the forefinger F by using the equation (3). In the present method, the finger-tapping force $F(\epsilon(t))$ is calculated by using the fingertips' stiffness function estimated (or produced) as shown in FIG. 5A and the fingertips' displacement $\epsilon(t)$ measured by using the magnetic sensors 101 and 102 as shown in FIG. 5C. The $F(\epsilon(t))$ is defined as the finger-tapping force. FIG. 5D shows a flow of process for estimating the finger-tapping force F by using the fingertips' stiffness function and the fingertips' displacement c.

Figure 6:
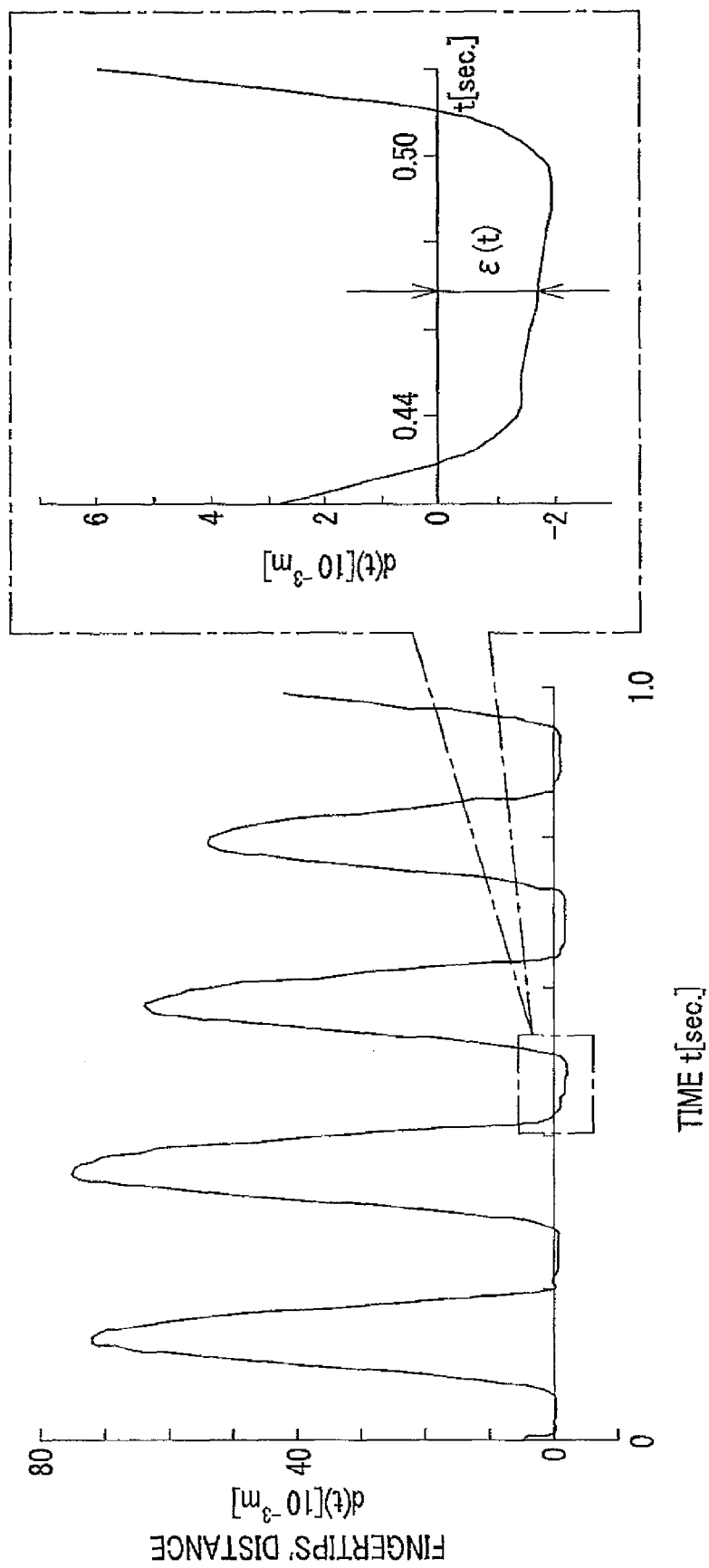
FIG. 6 shows an example of fingertips' distance obtained during the finger-tapping movement and measured as waveform by using the magnetic sensors.

FIG. 6 shows an example of fingertips' distance d(t) obtained during the finger-tapping movement and measured as waveform by using the magnetic sensors. According to the inventors' analysis, the fingertips of the thumb T and the forefinger F may be deformed very slightly upon making contact with each other in the finger-tapping movement, and at that time, the finger-tapping force is produced between the fingertips. The fingertips' distance d(t) can be measured by using the magnetic sensors 101 and 102. As shown in FIG. 6, the finger-tapping force is produced at the moment at which d(t) becomes equal to or lower than 0 (zero) [$10^{-3}$ m]. This state of d(t) lower than 0 (zero) [$10^{-3}$ m] is defined as c.

<Experiment for Estimating Fingertips' Stiffness Function and Finger-Tapping Force>

In order to evaluate the effectiveness of the present method, experiments are conducted for estimating the fingertips' stiffness function and the finger-tapping force. In the experiments, a subject person not affected by Parkinson's disease or other cerebral apoplexies puts the magnetic sensors on his or her thumb T and forefinger F.

<Experiment for Estimating Fingertips' Stiffness Function>
<Conditions>

To start with, the subject person held the force sensor 141 with the two fingers weakly so that the finger pulps thereof may not be deformed. The subject person applied forces to the thumb T and the forefinger F gradually while consciously maintaining the two fingers in parallel. The fingertips' displacement E and the force produced therebetween in this state were measured. The sampling frequencies of the magnetic sensors 101 and 102 were set at 100 [Hz], and the sampling frequency of the force sensor 141 was set at 2000 [Hz]. The experiment was repeated five times.

<Result>

Figure 7:
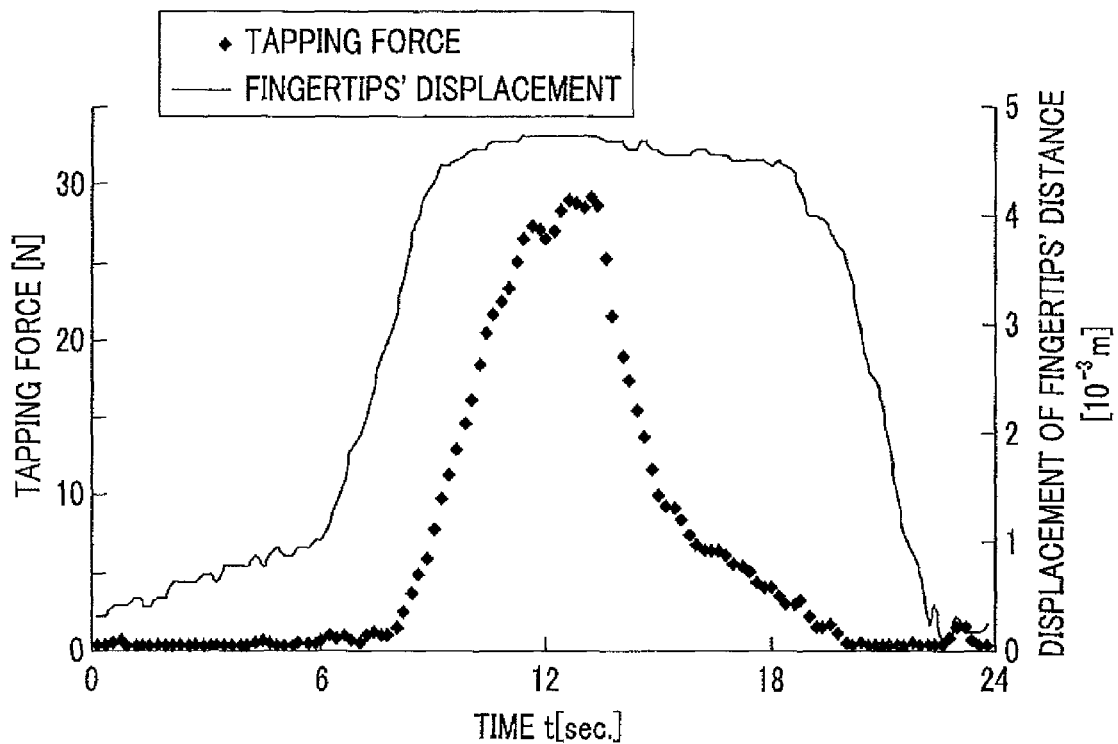
FIG. 7 shows an example of results obtained in the measurements.
Figure 8:
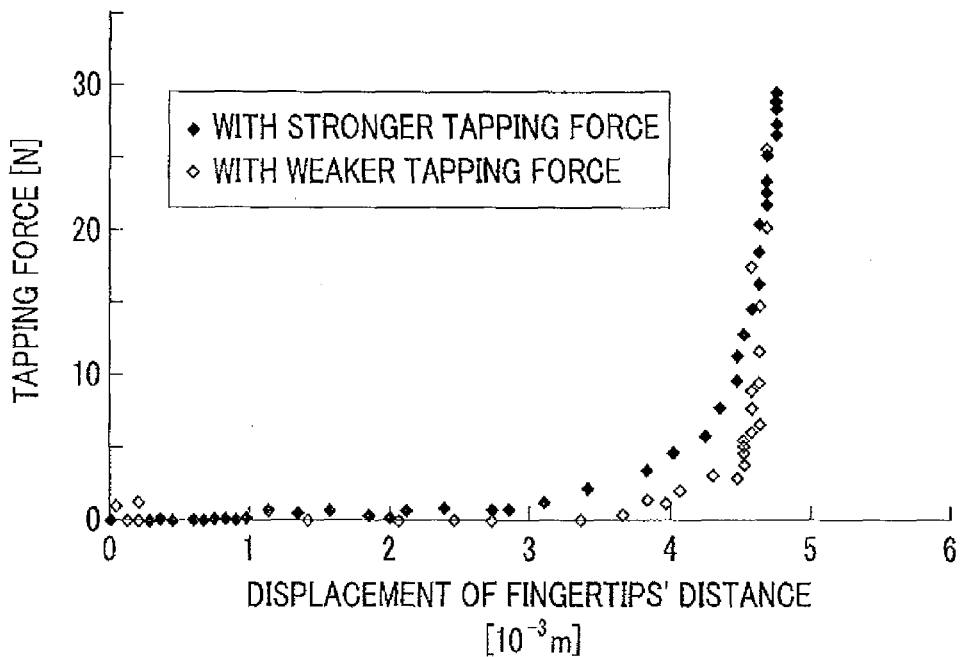
FIG. 8 shows an example of results obtained in the measurements.

FIGS. 7 and 8 show an example of measured displacement and force. In the graph of FIG. 7, the horizontal axis represents time; and the vertical axes represent the tapping force and displacement of the fingertips' distance. In the graph of FIG. 8, the horizontal axis represents the displacement of the fingertips' distance; and the vertical axis represents the tapping force produced by the two fingers.

Figure 10A:
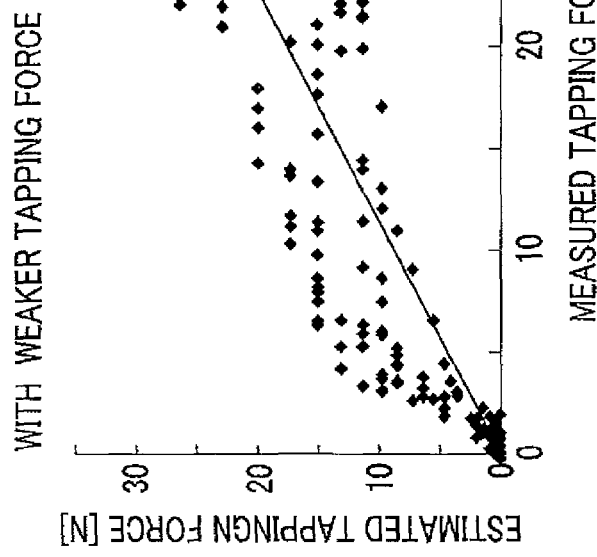
FIGS. 10A and 10B each show a correlation between an actual force measured by using a force sensor and an estimated force calculated in accordance with the displacement of the fingertips' distance.
Figure 10B:
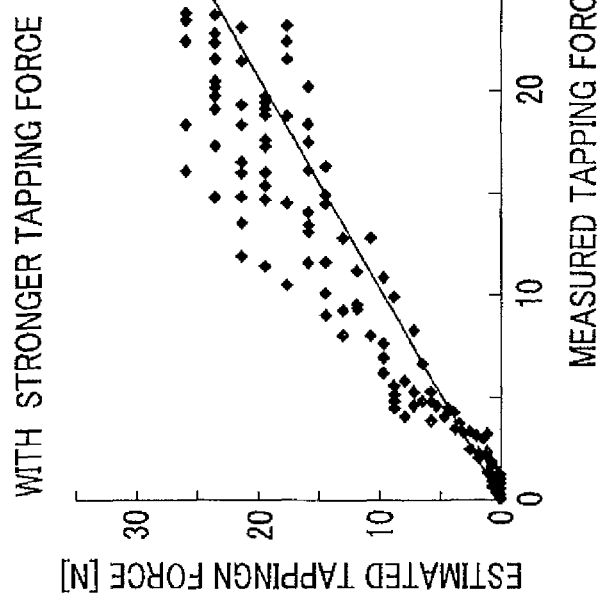

The graph in FIG. 7 reveals that the tapping force and the displacement of the fingertips' distance resemble in their profiles and degrees. The graph in FIG. 8 reveals that the tapping force and the displacement of the fingertips' distance differ in their profiles and degrees between one case applying a somewhat stronger force and another case applying a somewhat weaker force. FIGS. 9A and 9B are profiles of two slightly different tapping forces each obtained in five finger taps and varying over the displacement of the fingertips' distance. FIGS. 9A and 9B reveal that the plotted profiles of the tapping force and the displacement of the fingertips' distance have similar curves regardless of repetition of the experiment. Since these drawings show that the measured data vary exponentially, the finger-tapping force in the present embodiment can be defined by using the following equation (4):

$$F(\epsilon)=\alpha(e^{\beta\epsilon}-1) \quad \text{Equation (4)}$$

where α and β represent stiffness parameters determined by using non-linear least squares. In addition, FIGS. 9A and 9B each show an estimated curve of a fingertips' stiffness function plotted by using the equation (4). FIGS. 10A and 10B each show a correlation between an actual force measured by using a force sensor and an estimated force calculated in accordance with the displacement of the fingertips' distance. These drawings reveal that estimation conducted in the present invention was reliable since the correlation coefficient between the actually-measured force and the estimated force in the case of applying a somewhat stronger force was 0.96; and the correlation coefficient between the actually-measured force and the estimated force in the case of applying a somewhat weaker force was 0.88.

<Experiment for Estimating Finger-Tapping Force>
<Conditions>

The subject person putting the magnetic sensors 101 and 102 on the two fingers conducted the finger-tapping movement for 30 seconds and changed the force by every 10 seconds in order of weakly, slightly strongly, and strongly. In this experiment, the finger-tapping force was calculated from the displacement of the fingertips' distance produced when the two fingers made contact by using the previously estimated stiffness parameters α and β. The stiffness parameters α and β used for estimating the finger-tapping force were set appropriately in consideration of the case of applying a somewhat stronger force. (Alternatively, stiffness parameters α and β may be set appropriately in consideration of the two cases of applying a somewhat stronger force and a somewhat weaker force). Simultaneously, a muscle potential of the first dorsal interosseous (FDI) muscle conducting the finger-tapping movement was measured. The sampling frequencies of the magnetic sensors 101 and 102 were set at 100 [Hz], and the sampling frequency used for measuring the potential of the FDI muscle was set at 2000 [Hz]. The experiment was conducted once.

<Result>

Figure 11A:
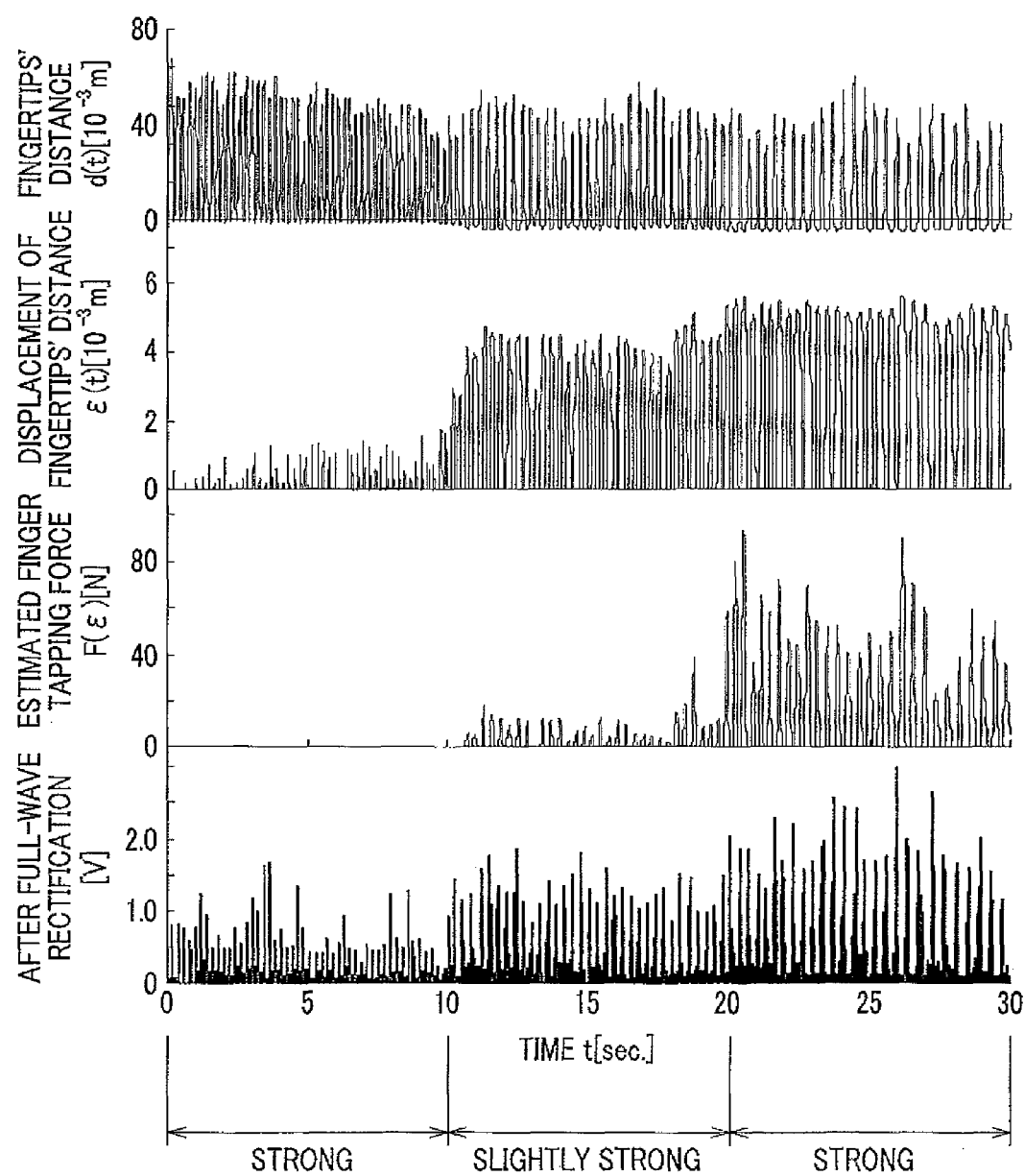
FIG. 11A shows an example of the result of estimating various parameters of the finger-tapping force.
Figure 11B:
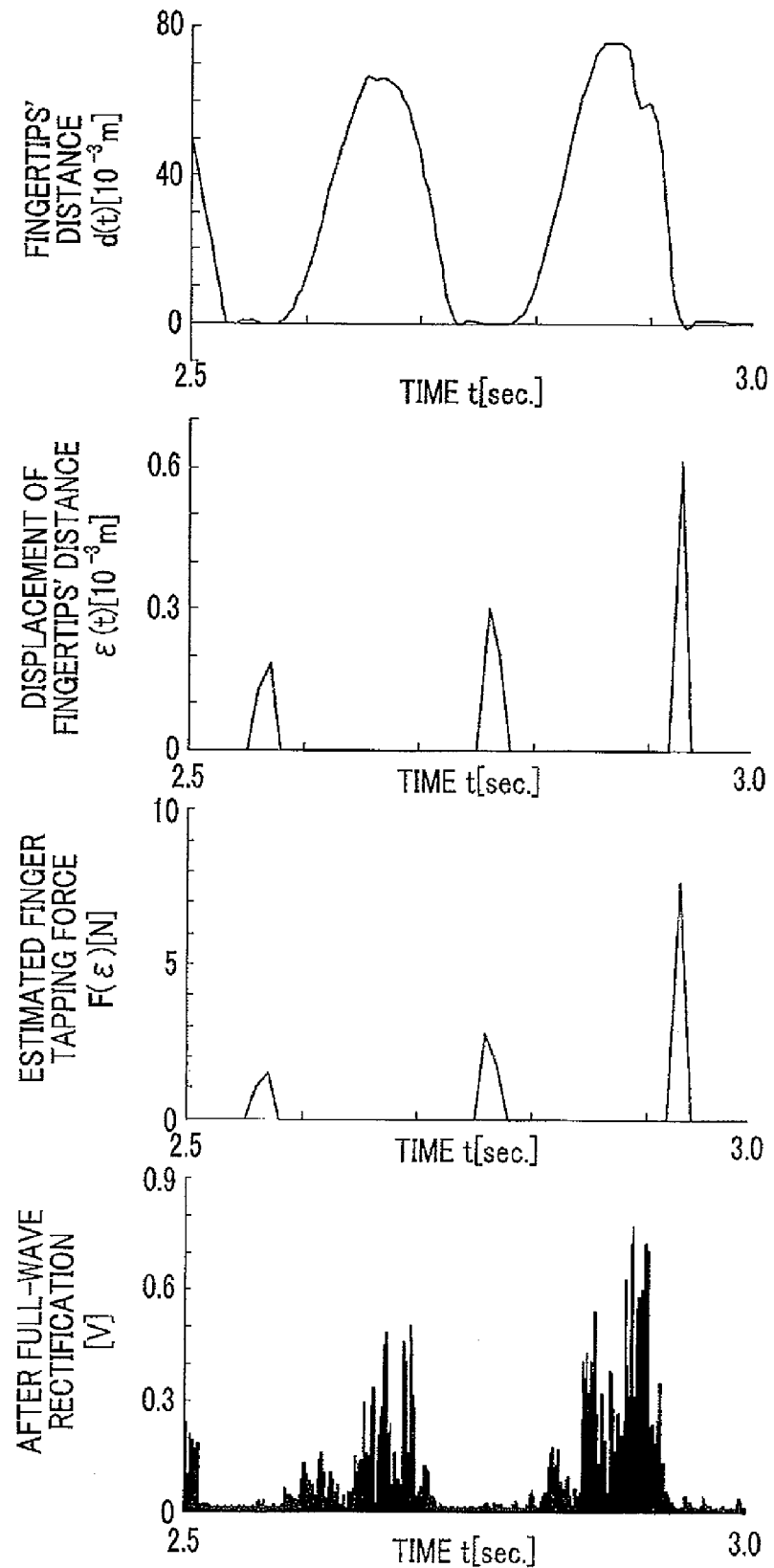
FIG. 11B shows graphs of the parameters described in a portion of a time frame shown in FIG. 11A and obtained with a "weak" tapping force.
Figure 11C:
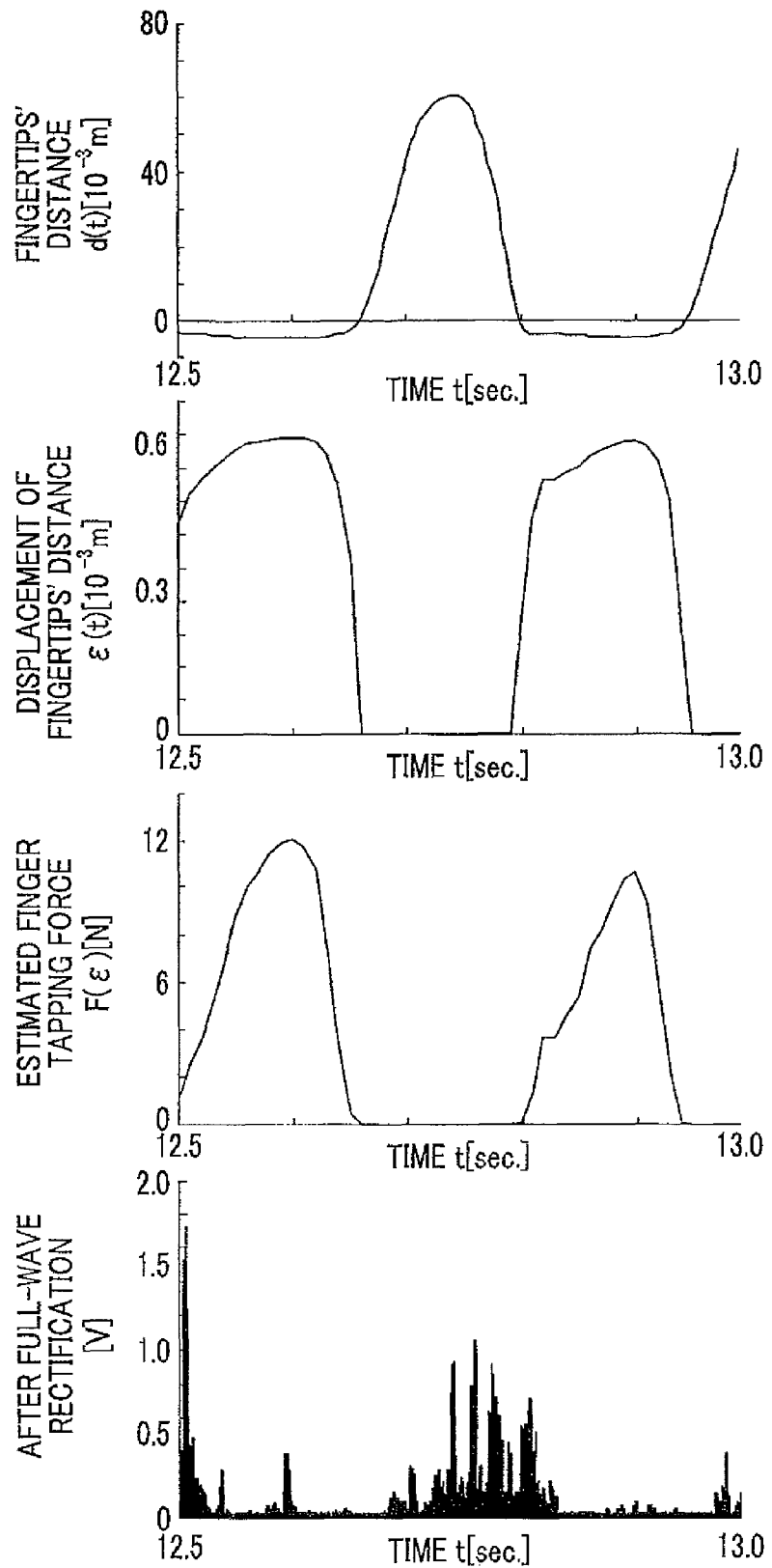
FIG. 11C shows graphs of the parameters described in the portion of the time frame shown in FIG. 11A and obtained with a "slightly strong" tapping force.

FIG. 11A shows an example of the result of estimating the finger-tapping force. Four graphs in FIG. 11A show, in order of: fingertips' distance; displacement of the fingertips' distance obtained when the fingertips make contact; estimated finger-tapping force; and a potential of the FDI muscle obtained after full-wave rectification. The graphs in FIG. 11A reveal that the displacement of the fingertips' distance and the estimated finger-tapping force increased if the finger-tapping force, produced when the two fingers were tapped, increased. Similarly, the graphs reveal that the potential of the FDI muscle varied in accordance with the magnitude of the finger-tapping force. FIG. 11B shows graphs of the parameters described in a portion of a time frame shown in FIG. 11A in an enlarged view and obtained with a "weak" tapping force. FIG. 11C shows graphs of the parameters described in the portion of the time frame shown in FIG. 11A in an enlarged view and obtained with a "slightly strong" tapping force. FIG. 11D shows graphs of the parameters described in the portion of the time frame shown in FIG. 11A in an enlarged view and obtained with a "strong" tapping force. The inventors of the present application comprehended that tendency for the finger-tapping force can be estimated by measuring the displacement of the fingertips' distance by using the magnetic sensors.

Figure 12A:
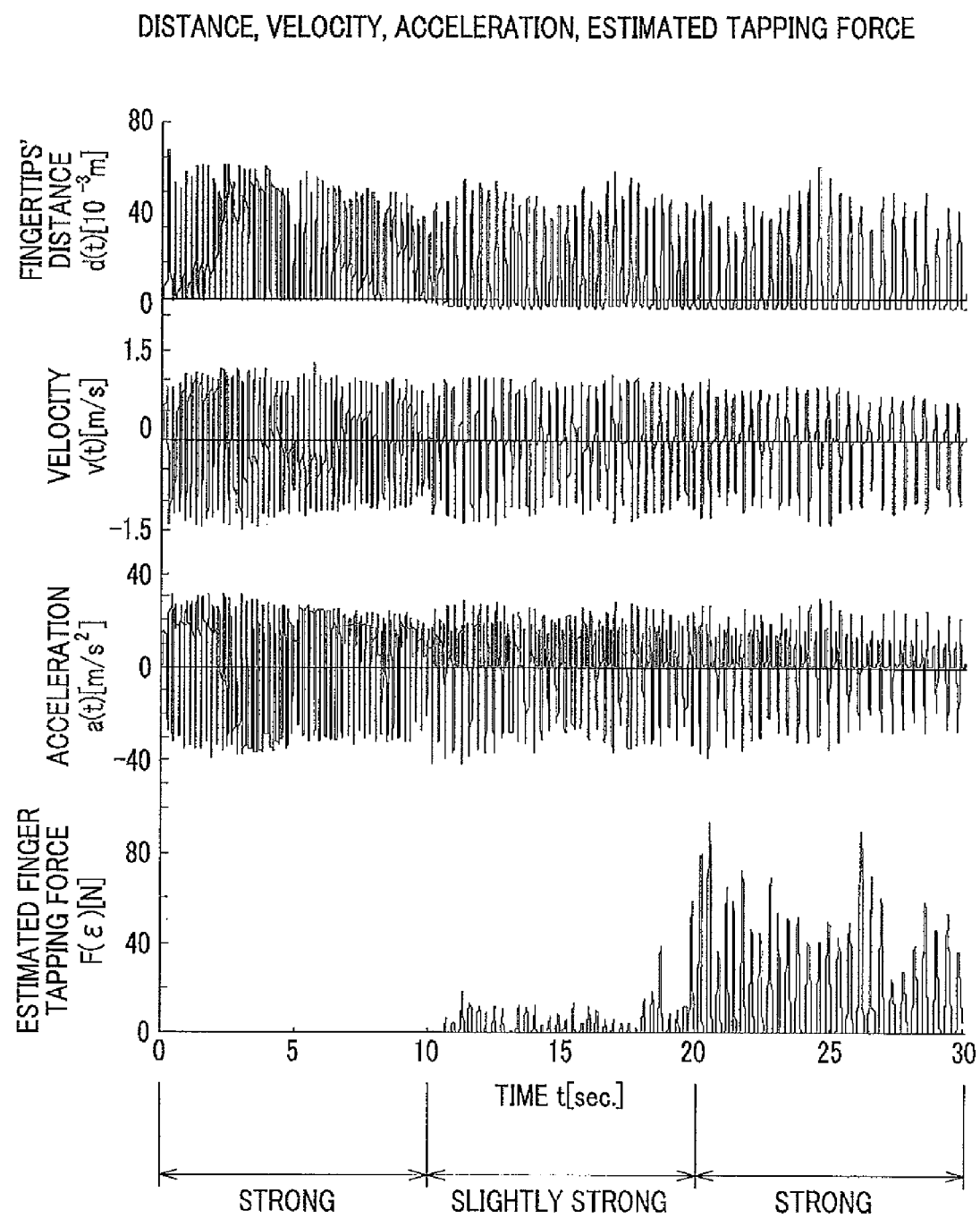
FIG. 12A shows an example of the result of estimating the finger-tapping force.
Figure 12B:
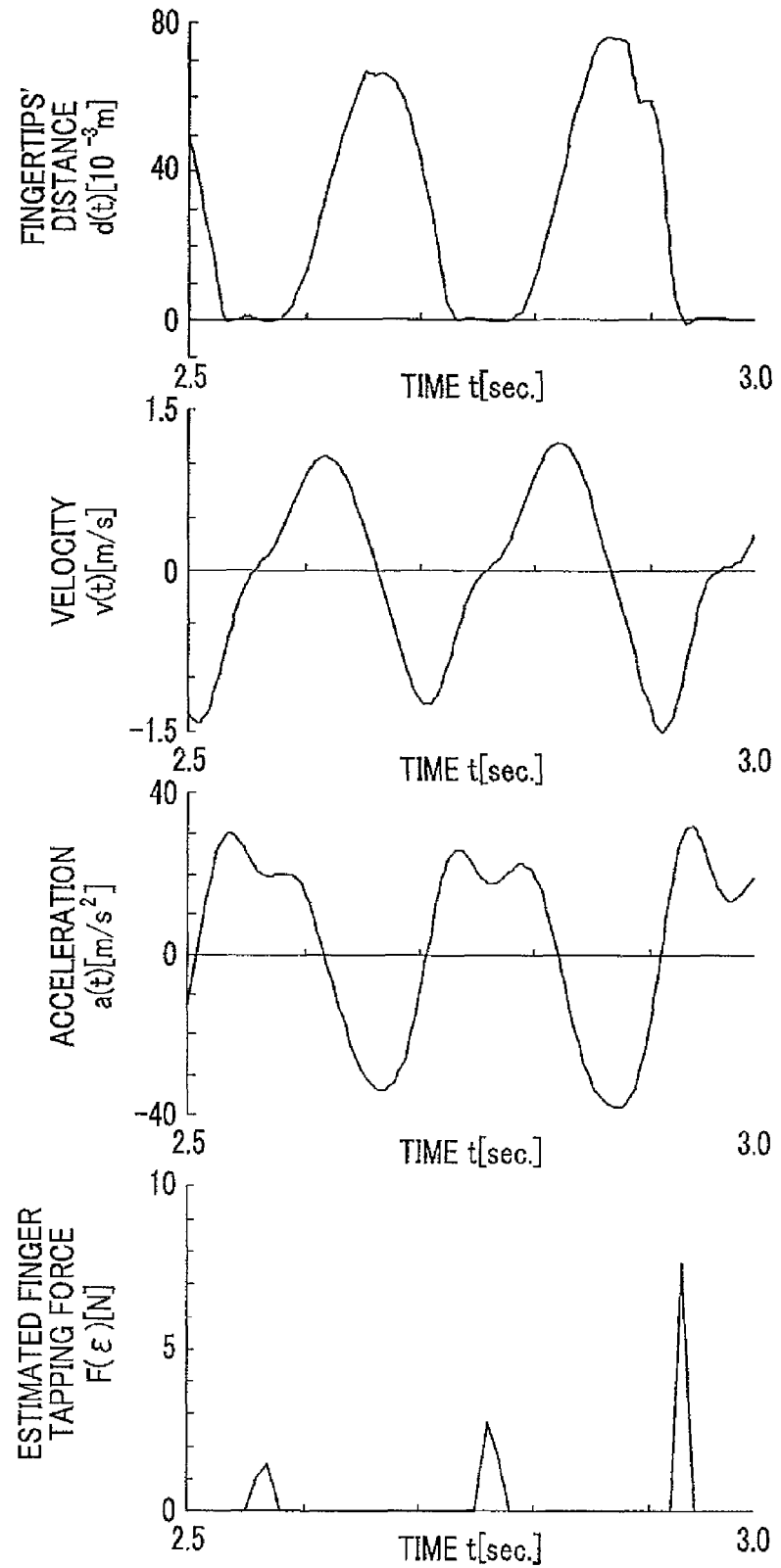
FIG. 12B shows graphs of the parameters described in a portion of a time frame shown in FIG. 12A and obtained with a "weak" tapping force.
Figure 12C:
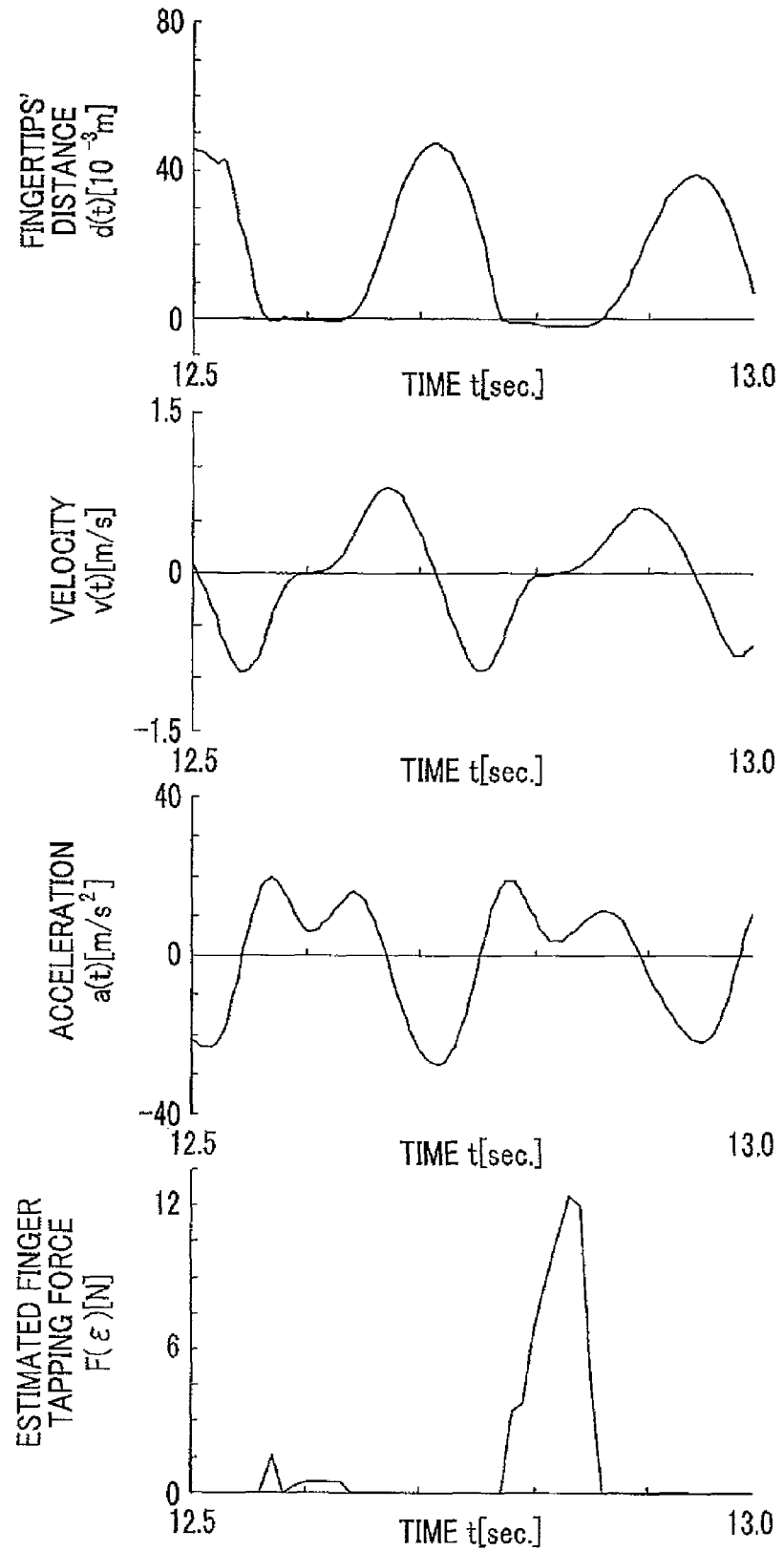
FIG. 12C shows graphs of the parameters described in the portion of the time frame shown in FIG. 12A and obtained with a "slightly strong" tapping force.
Figure 12D:
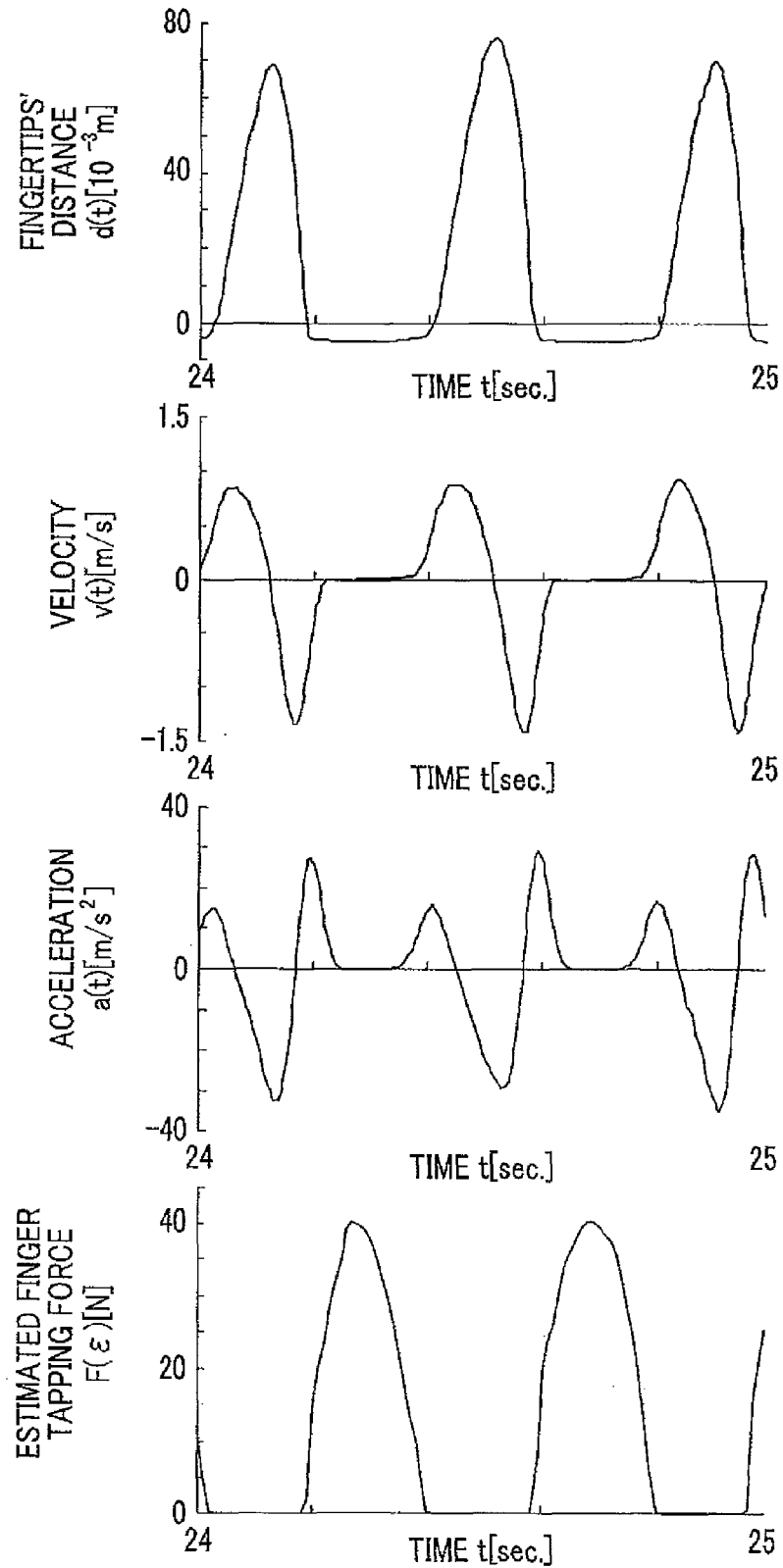
FIG. 12D shows graphs of the parameters described in the portion of the time frame shown in FIG. 12A and obtained with a "strong" tapping force.

FIG. 12A shows an example of the result of estimating the finger-tapping force. Four graphs in FIG. 12A show, in order of: the fingertips' distance; the (relative) velocity; the (relative) acceleration; and the estimated finger-tapping force. FIG. 12B shows graphs of the parameters described in a portion of a time frame shown in FIG. 12A in an enlarged view and obtained with a "weak" tapping force. FIG. 12C shows graphs of the parameters described in the portion of the time frame shown in FIG. 12A in an enlarged view and obtained with a "slightly strong" tapping force. FIG. 12D shows graphs of the parameters described in the portion of the time frame shown in FIG. 12A in an enlarged view and obtained with a "strong" tapping force.

In the present invention, profiles over time can be observed for the fingertips' distance; the (relative) velocity; the (relative) acceleration; and the estimated finger-tapping force by displaying graphs similar to those shown in FIGS. 12A to 12D on the display unit 124 of the bioinstrument device 108. When displaying those data, an average of estimated finger-tapping forces, an average of the finger-tapping forces of non-diseased persons; and an average of the finger-tapping forces of neurological disorder patients may be displayed additionally. The Identification (ID), name, gender, age, and inspection date for a subject person may be displayed additionally.

A bioinstrument system S according to the present embodiment can calculate and display a finger-tapping force by calculating a fingertips' distance based on information obtained by using the magnetic sensors 101 and 102; and by using a predetermined fingertips' stiffness function (i.e. equation (4)) and information indicative of variation of deformation of the two fingers, included in the calculated fingertips' distance. Therefore, whether a person suffers from a neurological disorder or not can be determined very accurately by an inspector e.g. a doctor because he or she can observe information of not only the two finger's movement in the finger-tapping movement but also the finger-tapping force. In addition, the information of the finger-tapping force may encourage a subject person in rehabilitation.

Although a predetermined fingertips' stiffness function should preferably be set separately for an opening movement and a closing movement of the two fingers in the finger-tapping movement, the estimation using a coefficient set for opening the two fingers will be also accurate to almost the same degree.

The inventors of the present application comprehends that the present invention can enhance the accuracy of the estimated finger-tapping force since an estimated force will be more realistic by including an exponential function in a predetermined fingertips' stiffness function.

Using the magnetic sensors for detecting the finger-tapping movement is more advantageous than using acceleration sensors since the bioinstrument system S is hardly affected by noise produced from the whole body of a subject person.

The explanation for the present embodiment is concluded, and it should be noted that the present invention is not limited to the aforementioned embodiment.

For example, the present invention can be used effectively not only in inspection conducted for neurological disorders but also in inspection conducted for degenerative diseases e.g. rheumatism.

Specific configuration of hardware and programs etc. can be modified arbitrarily within the range or spirit of the present invention.

What is claimed is:

1. A method implemented via a hardware processor, for determining a finger-tapping force in a finger-tapping movement of two fingers of one of a subject's hands by using a bioinstrument device equipped with a set of distance sensors deriving an output relating to a distance between the two fingers, the finger tapping force being a pushing force of the two fingers upon making contact with each other, the method comprising:

measuring stiffness characteristics of finger pulps of said two fingers by using the distance sensors and a force sensor as the subject pinches the force sensor with said two sensors;

estimating a stiffness function of the finger pulps;

registering the stiffness function in a storage unit;

obtaining a transitional change of the output of the distance sensors along a test period while the subject keeps on tapping said fingers;

extracting information indicative of a sum of displacements of the two fingers in a deformed state within the finger tapping movement, from the transitional change of the output of the distance sensors; and determining the finger-tapping force by using the information indicative of the sum of displacements and the finger pulps' stiffness function retrieved from the storage unit;

wherein at least one of the estimating, the registering, the obtaining, the extracting and the determining, are effected via the hardware processor.

2. The method for estimating the finger-tapping force as claimed in claim 1, wherein the method uses the two different finger pulps' stiffness functions separately estimated and registered for opening the two fingers and closing the two fingers in the finger-tapping movement.

3. The method for estimating the finger-tapping force as claimed in claim 1, wherein the finger pulps' stiffness function which is estimated in said estimating includes an exponential function.

* * * * *